United States Patent [19]

Bianco

[11] Patent Number: 5,348,747
[45] Date of Patent: Sep. 20, 1994

[54] PHARMACEUTICAL COATING SUGARS

[75] Inventor: Giustino Bianco, Newfield, N.J.

[73] Assignee: American Home Products Corporation, Madison, N.J.

[21] Appl. No.: 11,844

[22] Filed: Feb. 1, 1993

Related U.S. Application Data

[63] Continuation of Ser. No. 847,151, Mar. 5, 1992, abandoned.

[51] Int. Cl.$^5$ .................................................. A61K 9/16
[52] U.S. Cl. ..................................... 424/490; 424/469; 424/488; 424/489
[58] Field of Search ................ 424/490, 469, 488, 489

[56] References Cited

U.S. PATENT DOCUMENTS

| | | | |
|---|---|---|---|
| 2,921,883 | 1/1960 | Reese et al. | 167/82 |
| 3,446,891 | 5/1969 | Cavalli et al. | 424/34 |
| 4,177,254 | 12/1979 | Khan et al. | 424/16 |
| 4,371,516 | 2/1983 | Gregory et al. | 424/495 |
| 4,749,575 | 6/1988 | Rotman | 424/440 |
| 4,810,501 | 3/1989 | Ghebre-Sellassie | 424/469 |
| 4,820,523 | 4/1989 | Shtohryn et al. | 424/469 |
| 4,904,477 | 2/1990 | Ho et al. | 424/465 |
| 4,946,684 | 8/1990 | Blank et al. | 424/441 |
| 5,084,287 | 1/1992 | Ghebre-Sellassie et al. | 424/461 |
| 5,085,865 | 2/1992 | Nayak | 424/470 |
| 5,096,714 | 3/1992 | Kuhrts | 424/439 |

FOREIGN PATENT DOCUMENTS

| | | |
|---|---|---|
| 0253684 | 7/1987 | European Pat. Off. . |
| 2458112 | 12/1974 | Fed. Rep. of Germany . |
| 2241889A | 2/1991 | United Kingdom . |

*Primary Examiner*—Thurman K. Page
*Assistant Examiner*—W. Benston
*Attorney, Agent, or Firm*—John W. Routh

[57] ABSTRACT

A finely divided solid pharmaceutical dosage form for oral administration dissolved or suspended in a pharmaceutically acceptable liquid is described which pharmaceutical dosage form consists of a pharmaceutical coating on a sugar core.

11 Claims, No Drawings

PHARMACEUTICAL COATING SUGARS

This is a continuation of copending application Ser. No. 07/847,151 filed on Mar. 5, 1992, now abandoned.

This invention relates to solid pharmaceutical or medicament coated sugars which are essentially water soluble, the coating material being applied as a liquid to the solid sugar such that the sugar is wetted and partially dissolved by the coating material, and then dried. The pharmaceutical coated sugars are for oral administration dissolved in hot or cold water or other pharmaceutically acceptable liquid.

BACKGROUND OF THE INVENTION

Sugar coated pharmaceuticals are old in the art, the sugar coating generally being used to mask the taste of the usually insoluble pharmaceutical core. The sugar coating, however, is usually applied to a core which has previously been coated with a sealing coat to prevent inter mixture of the pharmaceutical containing core and the sugar coat. Note, for example, Example 12 of U.S. Pat. No. 4,904,477 to Hoet al.

Other patents of interest are U.S. Pat. No. 4,946,684 to Blank et al and U.S. Pat. No. 4,371,516 to Gregory et al described therein. These patents deal with Fast Dissolving Dosage Forms comprising an open matrix network carrying a pharmaceutical, wherein the open matrix network is comprised of a water-soluble or water-dispersable carrier material. The carrier material can be gelatin, hydrolysed dextran, dextrin or mannitol. The carrier material and the pharmaceutical, which can be chlorpheniramine maleate, are dissolved or dispersed in water, and the solution or admixture is freeze dried to form solid dosage forms.

Many patents exist which disclose coating of nonpareil seeds, i.e. sugar pellets, with a pharmaceutical as a first step in the preparation of a core for further processing to make sustained release medicaments. Such patents include U.S. Pat. Nos. 2,921,883 and 4,810,501, the first of which discloses in Example 3 the coating of nonpareil seeds in a coating pan with a coating solution, formed by dissolving chlorprophenpyridamine maleate in a 10% gelatin solution, to form drug pellets which are then coated with a fat-cellulosic coating solution to form a delayed release medicament. U.S. Pat. No. 4,810,501 discloses in the example the spray coating of nonpareil seeds with a coating solution formed by mixing with water kaolin, diphenhydramine hydrochloride and hydroxypropyl cellulose. The drug layered pellets were then coated with ethyl cellulose to form sustained release pellets. The pharmaceutical dosage forms of this invention, however, are for intermediate release.

U.S. Pat. No. 4,177,254 discloses solid penicillin dosage forms wherein an aqueous suspension of a penicillin and a binder is sprayed onto a fluidized bed comprising sucrose. The binder can be sucrose such that the binder admixed with the insoluble penicillin forms a layer on the sucrose particles in the fluidized bed, which layer comprises particles of penicillin dispersed throughout the binder. The solid dosage forms can be reconstituted with water to form a syrup.

SUMMARY OF THE INVENTION

This invention is an improved solid pharmaceutical dosage form for oral administration dissolved or suspended in a liquid and having a sugar core the surface of which has been wetted with an aqueous base pharmaceutical coating solution and then dried such that the surface of the sugar core is dissolved and intimately admixed with the coating solution thereby forming an intimate bond between the core and the pharmaceutical upon drying. The sugar core consists essentially of about 90% to 100% by weight of sugar based on the weight of the sugar core., the sugar core comprising about 90% to about 99% by weight of the pharmaceutical dosage form. The pharmaceutical coating consists essentially of about 25% to about 50% by weight of sugar based on the weight of the coating and about 50% to about 75% by weight of pharmaceutical based on the weight of the dry coating, and the dry coating comprises about 1% to about 5% by weight of the pharmaceutical dosage form. The pharmaceutical coating is applied by pan coating to the sugar core from an aqueous solution of the sugar and a water-soluble pharmaceutical containing about 50% to about 80% by weight of water, preferably at least about 70% by weight of water. Too much water requires a longer processing time and too little water inhibits formation of the intimate bond between the sugar core and the water soluble pharmaceutical upon drying.

DETAILS OF THE INVENTION

The pharmaceuticals or medicaments useful in the invention include, for example, nonnarcotic analgesics such as acetaminophen; antihistamines such as terrenadine, chlorpheniramine maleate, phenylephrine hydrochloride, diphenhydramine hydrochloride, bromopheniramine maleate and pheniramine maleate; nonsteroidal antiinflammatories such as ibuprofen, ketoprofen, etodolac and indomethacin; decongestants such as pseudoephedrine hydrochloride, phenylpropanolamine hydrochloride and ephedrine hydrochloride; cough suppressants such as dextromethorphan hydrobromide and guaifenesin; bronchodilators such as epinephrine, isoproterenol hydrochloride and theophylline; and stimulants such as caffeine.

When more than one pharmaceutical is employed, they may be divided between the pan charge and the coating solution. The water-soluble pharmaceuticals are used as an ingredient of the coating solution and water-insoluble or difficulty dispersable pharmaceuticals are used as an ingredient with sugar in the pan charge. The water-soluble pharmaceuticals generally include the acid addition salts, i.e. the inorganic and organic acid addition salts such as the hydrochlorides, the hydrobromides and the maleates. The nonnarcotic analgesics and the antiinflammatories generally have limited solubility, as do terrenadine and epinephrine. Since the coating solution is at least about 70% water and relatively large proportions are used, pharmaceuticals such as guaifenesin and theophilline can be used since they are soluble to the extent required especially in warm water. At about 50° to 60° C. guaifenesin is quite soluble in such warm-water and does not precipitate out at lower temperatures of about 25° C. Accordingly, water-soluble pharmaceuticals are those that are soluble to an extent such that 12 to 20 grams of the final pharmaceutical dosage form will provide an adequate adult dosage of the water-soluble pharmaceutical.

In addition to the sugar and the pharmaceuticals, the pan charge can contain a water-soluble polymer to promote agglomeration of the sugar particles. Such polymers useful in this invention include water soluble polymers which are nontoxic and pharmacologically acceptable, particularly for oral administration. Illustrative of such polymers are polyvinylpyrrolidone, hydroxypropyl methyl cellulose, hydroxypropyl cellulose, methyl cellulose, block co-polymers of ethylene oxide and propylene oxide and polyethylene glycol. Other polymers include the natural gums such as xanthan gum, karaya gum, and the like.

Similarly the coating solution can contain other watersoluble ingredients such as colors, flavors, binders, and the like, in addition to the pharmaceutical.

After the coating step is completed, water-insoluble agents such as anticaking agents can be added. These include colloidal silicon dioxide and tricalcium phosphate. Also flavoring agents such as citric acid can be added at this point.

The sugars useful in the invention include sucrose, dextrose, glucose, fructose, lactose, and mannose. Sucrose is the preferred sugar primarily because of its availability and low cost. The weight ratio of sugar to pharmaceutical is about 90:10 to about 98:2 such that the amount of a single adult dose of the dosage form of the invention will be about 12 to 20 grams, an amount that can readily be mixed with or dissolved in the pharmaceutically acceptable liquid, and can be packaged in individual sachet dosages.

The invention will now be further described in the following examples.

EXAMPLE 1

In the following example a finely divided solid dosage form was prepared having three pharmaceutical ingredients. The charge to the coating pan contained acetaminophen in addition to the sucrose and the coating solution contained pseudoephedrine HCl and dextromethorphan HBr as well as the sucrose. The coating pan was a 60 inch Pellegrini Model T-300 and the pump for the coating solution was a Graco-Monark 5:1 airless sprayer equipped with an 0.017 inch tip and with an 18 inch fan width delivering approximately 380–400 ml of coating solution per minute. The drying air inlet temperature was set at 50° C. and full air flow was 2100 feet per minute and partial air flow was 1100 feet per minute. The coating pan was set to rotate at 12RPM.

The ingredients used were as follows:

| Pan Charge: | Sucrose Cane NF (extra fine) 30–60 mesh | 244 kg |
|---|---|---|
| | Hydroxypropylmethylcellulose E-5 (HPMC) | 512 g |
| | Compap L (90% Acetaminophen) | 9,074 g |

The sucrose comprised about 95.9% of the pan charge and the pharmaceutical comprised about 3.2%.

| Coating Solution: | Pseudoephedrine, HCl | 1,008 g |
|---|---|---|
| | Dextromethorphan HBr | 504 g |
| | Sucrose, Cane NF (extra fine) 30–60 mesh | 1,008 g |
| | Water | 7,560 g |
| | Appearance: Clear Solution | |

The sucrose comprised about 40% of the coating solids and the pharmaceutical comprised about 60% of the coating solids.

The 60" Pellegrini Pan was prewarmed for 20 minutes with full air (50° C.) and then charged with sucrose, Compap L and HPMC. With the door cover "on" and exhaust outlet "off" the batch was then tumbled for five (5) minutes at 12 RPM to insure a uniform dry blend before the start of the spraying process.

The goal of the spraying process was to apply the coating solution as fast as possible to keep the batch as wet as possible without triggering the formation of sugar lumps.

The coating cycles, all at 12 RMP, were as follows and the total process time for coating was 127.5 minutes.

| CYCLE # | Spray Time | NO AIR Tumble | Full Air | Part Air |
|---|---|---|---|---|
| 1 | 8' 00" | 3' 00" | 8' 00" | — |
| 2 | 4' 00" | 2' 00" | 9' 00" | — |
| 3 | 4' 30" | 2' 00" | 17' 00" | — |
| 4 | 2' 30" | 2' 00" | 7' 00" | — |
| 5 | 2' 00" | 1' 00" | 4' 00" | — |
| 6 | 2' 00" | 1' 30" | 13' 00" | — |
| 7 | — | — | 30' 00" | (40° C.) 5' 00" (40° C.) |

The coated core through Cycle #7 comprised about 95.4% by weight of sucrose and about 4.1% by weight of pharmaceutical.

At the end of Cycle #7, the moisture content was 0.21%. At this point anticaking additives were added, colloidal silicon dioxide in the amount of 128 grams and tricalcium phosphate in the amount of 384 grams. After tumbling for an additional 5 minutes, the moisture content was 0.15%. The total yield was 250 kilograms, i.e. about 98%.

The product was subjected to a screen analysis, i.e. a 100 gram sample, Rotap, for 5 minutes, and is compared to a screen analysis of the sucrose raw material as follows:

| | 14 Mesh | 20 | 30 | 40 | 60 | 80 | Pan |
|---|---|---|---|---|---|---|---|
| Typical Sucrose: | 0 | Trace | 13 | 40 | 42 | 4 | 1 |
| Experiment Batch: | 0 | 2.7 | 32 | 51 | 14 | 0.2 | Trace |

Due to agglomeration of sugar grains during the coating process, the comparison set forth above indicates a shift from the finer to the coarser end. This is a clear indication that the water from the coating solution is not only dissolving the surface of the substrate but also causing a bond between the grains as well.

EXAMPLE 2

In the following example a finely divided solid dosage form of the invention was prepared having four pharmaceutical ingredients. The charge to the coating pan contained acetaminophen in addition to the sucrose, and the coating solution contained pseudoephedrine hydrochloride, diphenylhydramine hydrochoride and dextromethorphan hydrochloride as well as the sucrose. The equipment was the same as that used in Example 1.

P The ingredients used were as follows;

| Pan Charge: | Sucrose, Cane NF (30–60 mesh) | 233 kg |
|---|---|---|
| | Hydroxypropylmethyl cellulose E-5 (HPMC) | 600 g |
| | Compap L (90% Acetaminophen) | 13600 g |

The sucrose comprises about 94.3% of the pan charge and the pharmaceutical comprises about 4.9% of the pan charge.

| Coating Solution: | Pseudoephedrine, HCl | 750 g |
|---|---|---|
| | Diphenylhydramine HCl | 630 g |
| | Dextromethorphan HBr | 378 g |
| | D & C Yellow #10 | 3024 mg |
| | FD & C Yellow #6 | 636 mg |
| | Sucrose, Cane NF | 756 g |
| | Water | 7560 ml |

The sucrose comprised about 30% of the coating solids and the pharmaceuticals comprised about 70% of the coating solids.

| Sweetener Blend: | Sucrose, Cane NF | 720 g |
|---|---|---|
| | Nutrasweet | 730 g |
| | Blended in bag for 1 minute | |
| Flavor Blend; | Sucrose, Cane NF | 3360 g |
| | Natural Lemon Flavor #16774 | 900 g |
| | Natural Honey Flavor | 1200 g |

| Flavor/Anticaking Blend: | Citric Acid, Fine Granular | 7200 g |
|---|---|---|
| | Tri Calcium Phosphate | 288 g |
| | Colloidal Silicon Dioxide | 144 g |

The 60" Pellegrini pan was prewarmed for 20 minutes with full air (50° C.) and then charged with sucrose, Compap L and HPMC. With the door cover "on" and exhaust outlet "off" the batch was then tumbled for five (5) minutes at 12 RPM to insure a uniform dry blend before the start of the spraying process.

The water was heated in a 30 gallon kettle to 55°-60° C. and there were dissolved therein the dyes, all of the sucrose, the diphenylhydramine hydrochloride, the dextromethorphan hydrobromide and the pseudoephedrine hydrochloride and the admixture was mixed to a clear solution. The coating solution was held at a temperature of above 22° C. until application.

The goal of the spraying process was to apply the coating solution as fast as possible to keep the batch as wet as possible without triggering the formation of sugar lumps.

The drying air inlet temperature was set at 50° C. and full air flow was 2100–2200 feet per minute, partial air flow was 1500–1600 feet per minute, and exhaust was 800 feet per minute.

The coating cycles, all at 13 RPM, were as follows and the total process time for coating was about 156.5 minutes.

| Step # | Spray Time | No Air Tumble | Full Air | Partial Air |
|---|---|---|---|---|
| 1 | 8' 00" | 3' 00" | 12' 00" | — |
| 2 | 4' 00" | 2' 00" | 16' 00" | — |
| 3 | 4' 00" | 2' 00" | 12' 00" | — |
| 4 | Sprinkle sweetener blend | | | |
| | | 2' 00" | (Exhaust open) | |
| 5 | 3' 00" | 2' 00" | 12' 00" | |
| 6 | Sprinkle lemon blend | | | |
| | | 3' 00" | (Exhaust open) | |
| 7 | 2' 00" | 1' 30" | 9' 30" | |
| 8 | Sprinkle honey flavor blend | | | |
| | | 3' 00" | (Exhaust open) | |
| 9 | 3' 00" | 1' 30" | 17' 00" | |

10. Sprinkle 15 kg sucrose over a period of 3 minutes with no air tumbling, exhaust open, for dusting purposes, at a pan speed of 9RPM.

11. Partial air drying for 30 minutes at 9RPM and at the end of cycle 11 the moisture content was 0.28% but after an additional ten minutes with partial air tumbling, the moisture content was 0.09%.

12. The flavor/anticaking blend was added to the batch with tumbling for five minutes at 13 RPM.

13. The pan was unloaded and the batch was screened through a #10 mesh screen and no lumps were observed. The yield was 259 kg, i.e. 98%.

After about 13–14 minutes of full air during step 9, some sticking was noticed on the pan sides. This sticking was alleviated by the dusting step 10 and the problem disappeared.

The coated core through step 9 comprised about 93.6% by weight of sucrose and about 5.6% by weight of pharmaceutical. The finished dosage form through step 11 comprised about 92.97% by weight of sucrose and about 5.15% by weight of pharmaceutical.

I claim:

1. A finely divided water soluble solid pharmaceutical dosage form having a particle size smaller than 10 mesh for immediate release of the pharmaceutical by oral administration of a pharmaceutically acceptable liquid having the water-soluble solid pharmaceutical dosage form dissolved therein, the pharmaceutical dosage form consisting of a pharmaceutical coating on a sugar core wherein:
   a) the sugar core consists essentially of about 90% to 100% by weight of sugar based on the weight of the sugar core, the sugar having a particle size of 30–60 mesh and the sugar core comprising about 90% to about 99% by weight of the pharmaceutical dosage form;
   b) the pharmaceutical coating consists essentially of about 25% to about 50% by weight of sugar based on the dry weight of the coating and about 50% to about 75% by weight of at least one water-soluble pharmaceutical based on the dry weight of the coating and the coating comprising about 1% to about 5% by weight of the pharmaceutical dosage form; and
   c) the pharmaceutical coating having been applied to the sugar core from an aqueous solution of the sugar and the water-soluble pharmaceutical containing about 50% to 80% by weight of water by pan coating such that the surface of the sugar core is dissolved and intimately admixed with the coating solution thereby forming an intimate bond between the sugar core and the water-soluble pharmaceutical.

2. The finely divided solid pharmaceutical dosage form of claim 1 wherein the pharmaceutical coating contains at least one water-soluble medicament selected from the group consisting of antihistamines, decongestants, cough suppressants and bronchodilators.

3. The finely divided solid pharmaceutical dosage form of claim 1 wherein the sugar core additionally contains at least one medicament selected from the group consisting of nonnarcotic analgesics and nonsteroidal antiinflammatories.

4. The finely divided solid pharmaceutical dosage form of claim 1 wherein the sugar is sucrose and the pharmaceutical coating having been applied to the sugar core from an aqueous solution of the sugar and the water-soluble pharmaceutical containing at least about 70% by weight of water.

5. The finely divided solid pharmaceutical dosage form of claim 4 wherein the pharmaceutical coating contains at least one water-soluble medicament selected from the group consisting of antihistamines, decongestants, cough suppressants and bronchodilators.

6. The finely divided solid pharmaceutical dosage form of claim 4 wherein the sugar core additionally contains at least one medicament selected from the group consisting of nonnarcotic analgesics and nonsteroidal antiinflammatories.

7. The finely divided solid pharmaceutical dosage form of claim 6 wherein the sugar core contains a nonnarcotic analgesic.

8. The finely divided solid pharmaceutical dosage form of claim 7 wherein the pharmaceutical coating contains at least one water-soluble medicament selected from the group consisting of antihistamines, decongestants and cough suppressants.

9. The finely divided solid pharmaceutical dosage form of claim 4 wherein the sugar core contains a nonnarcotic analgesic and the pharmaceutical coating contains at least one water-soluble medicament selected from the group consisting of antihistamines, decongestants and cough suppressants.

10. The finely divided solid pharmaceutical dosage form of claim 9 wherein the sugar core contains acetaminophen and the pharmaceutical coating contains pseudoephedrine hydrochloride and dextromethorphan hydrobromide.

11. The finely divided solid pharmaceutical dosage form of claim 9 wherein the sugar core contains acetaminophen and the pharmaceutical coating contains pseudoephedrine hydrochloride, diphenylhydramine hydrochloride and dextromethorphan hydrobromide.

* * * * *